United States Patent

Wiedemann et. al., deceased

Patent Number: 4,507,488
Date of Patent: Mar. 26, 1985

[54] N-PYRAZOLYLALKYLENEDIAMINE INTERMEDIATES

[75] Inventors: Fritz Wiedemann, deceased, late of Weinheim-Lutzelsachsen, Fed. Rep. of Germany, by Ingrid Wiedemann, curator; Ewald Rieger, Mannheim, Fed. Rep. of Germany

[73] Assignee: Boehringer Mannheim GmbH, Mannheim, Fed. Rep. of Germany

[21] Appl. No.: 483,788

[22] Filed: Apr. 11, 1983

Related U.S. Application Data

[63] Continuation-in-part of Ser. No. 273,295, Jun. 15, 1981, abandoned.

[30] Foreign Application Priority Data

Jun. 23, 1980 [DE] Fed. Rep. of Germany ....... 3023369

[51] Int. Cl.³ .......................................... C07D 231/38
[52] U.S. Cl. .................................. 548/362; 548/375; 548/377
[58] Field of Search ............... 548/365, 360, 362, 377, 548/375

[56] References Cited

U.S. PATENT DOCUMENTS 3,299,091 1/1967 Jucker et al. ........................ 548/362
3,615,506 10/1971 Abbott et al. ........................ 548/365

Primary Examiner—Henry R. Jiles
Assistant Examiner—Kurt G. Briscoe
Attorney, Agent, or Firm—Sprung, Horn, Kramer & Woods

[57] ABSTRACT

New N-heteroarylalkylenediamine

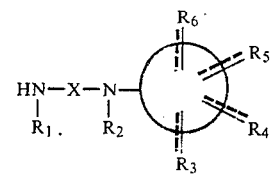

wherein
$R_1$ and $R_2$ each independently is hydrogen, an alkyl radical containing up to 6 carbon atoms, or a benzyl radical,
X is an alkylene radical containing 2 to 6 carbon atoms,
A is a mono- or bicyclic heteroaromatic radical, which can be partly hydrogenated, with the proviso that it contains 2 or 3 adjacent ring heteroatoms, whereby the bound ring heteroatoms can be an oxygen atom and a nitrogen atom or 2 or 3 nitrogen atoms, and
$R_3$, $R_4$, $R_5$, $R_6$ and $R_7$ each independently is hydrogen, or an alkyl radical containing up to 6 carbon atoms, which can be substituted by hydroxyl, carbamyl, nitrile or carboxyl, an alkenyl radical containing 2 to 6 carbon atoms, a phenyl or carbamyl radical or one of the divalent substituents oxygen or sulphur, or a salt thereof. The compounds are intermediates in the synthesis of cardioactive compounds.

5 Claims, No Drawings

N-PYRAZOLYLALKYLENEDIAMINE INTERMEDIATES

This is a continuation-in-part of application Ser. No. 273,295, filed June 15, 1981, now abandoned.

The present invention is concerned with new N-heteroarylalkylenediamines, which are valuable intermediates for the preparation of compounds which have a cardiac and circulatory activity, and is also concerned with the preparation of these new compounds.

Compounds of a similar structure are described as intermediates in Federal Republic of Germany Patent Specification No. 28 19 629.

The new N-heteroarylalkylenediamines according to the present invention are compounds of the general formula:

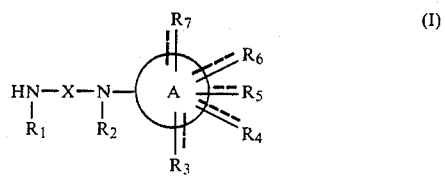

wherein $R_1$ and $R_2$, which can be the same or different, are hydrogen atoms or alkyl radicals containing up to 6 carbon atoms or benzyl radicals, X is a straight-chain or branched alkylene radical containing 2 to 6 carbon atoms, A is a mono- or bicyclic heteroaromatic radical, which can be partly hydrogenated, with the proviso that it contains 2 or 3 adjacent ring heteroatoms, whereby the bound ring heteroatoms can be an oxygen atom and a nitrogen atom or 2 or 3 nitrogen atoms and $R_3$, $R_4$, $R_5$, $R_6$ and $R_7$, which can be the same or different, are hydrogen atoms or alkyl radicals containing up to 6 carbon atoms, which can be substituted by hydroxyl, carbamyl, nitrile or carboxyl, or alkenyl radicals containing 2 to 6 carbon atoms or phenyl or carbamyl radicals or the divalent substituents oxygen or sulphur; and the salts thereof.

Since the compounds of general formula (I) can contain asymmetric carbon atoms, the present invention also includes the optically-active forms and racemic mixtures of these compounds.

Examples of monocyclic heteroaromatic radicals A present in the compounds (I) include radicals derived from isoxazole, pyrazole, 1,2,4-triazole and 1,2,4-triazine and examples of bicyclic heteroaromatic radicals A present in the compounds (I) include radicals derived from indazole, benztriazole, cinnoline, phthalazine and pyrazole[3,4-b]pyridine. The possibly hydrogenated heteroaromatic radical A can be, for example, the radical derived from pyrazoline. Other radicals can contain the divalent substituents oxygen or sulphur, for example, the radicals derived from pyrazol-3-one and triazin-3-one. A partly hydrogenated bicyclic heteroaromatic radical can be, for example, the radical derived from dihydroindazole which, as divalent substituent, can contain oxygen, for example the radical derived from indazol-3-one.

The attachment with the —X—N($R_2$)— chain can be not only on a cyclic carbon atom but also on a cyclic nitrogen atom of the heterocyclic moiety in question.

The lower alkyl radicals $R_1$, $R_2$, $R_3$, $R_4$, $R_5$, $R_6$ and $R_7$ are straight-chain or branched radicals containing up to 6 and preferably up to 4 carbon atoms, for example methyl, ethyl, isopropyl, butyl and n-hexyl radicals, methyl radicals being especially preferred.

The alkylene chain X is straight-chained or branched and contains 2 to 6 carbon atoms, the ethylene and propylene radicals being especially preferred.

In cases in which the radical A is a low substituted heterocyclic radical or has fewer than 6 ring atoms, some of the substituents $R_3$, $R_4$, $R_5$, $R_6$ and $R_7$ will not be present.

The new compounds (I) are useful intermediate for the preparation of compounds with valuable pharmacological properties, for example for the preparation of compounds with a cardiac and circulatory activity such as are described and claimed in patent application Ser. No. 273,543, filed June 15, 1981, now Pat. No. 4,438,128. Thus, for example, reaction of 4-(2-aminoethylamino)-1,3,5-trimethylpyrazole (see Example 16 hereinafter) with phenyl glycidyl ether gives the cardiotonically-active 1-phenoxy-3-[2-(1,2,3-trimethylpyrazol-4-ylamino)-ethylamino]-propan-2-ol (see Example 2 of application Ser. No. 273,543).

The new compounds (I) can be prepared, for example, by one of the following processes:

(a) reaction of a compound of the general formula:

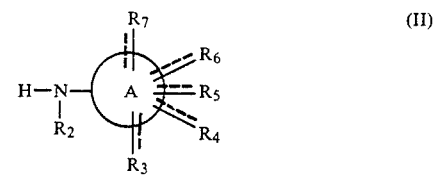

in which A, $R_2$, $R_3$, $R_4$, $R_5$, $R_6$ and $R_7$ have the same meanings as above, with a compound of the general formula:

in which X has the same meaning as above, Y is a reactive group and B is a protective group, followed by removal of the protective group; or (b) reaction of a compound of the general formula:

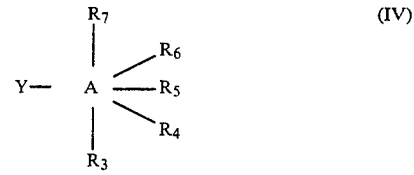

in which A, $R_3$, $R_4$, $R_5$, $R_6$ and $R_7$ have the same meanings as above and Y is a reactive group, with a compound of the general formula:

in which X, $R_1$ and $R_2$ have the same meanings as above; or (c) reaction of a compound of the general formula:

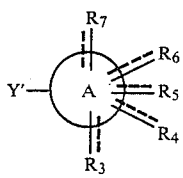

in which $R_3$, $R_4$, $R_5$, $R_6$ and $R_7$ have the same meanings as above, A' is a reactive heterocycle and Y' is a hydroxyl or amino group, with a compound of general formula (V), in which X, $R_1$ and $R_2$ have the same meanings as above, and which, in this case, are used in the form of their salts with sulphurous acid (Bucherer-Lepetit reaction); or (d) when $R_1$ represents $C_1$-$C_6$ alkyl or benzyl and X represents an ethylene group in a final product of general formula (I), reacting a compound of the general formula (VI)

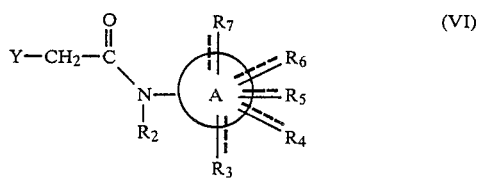

in which Y, $R_2$, $R_3$, $R_4$, $R_5$, $R_6$ and $R_7$ have the same meanings as above with $C_1$-$C_6$ alkylamine or benzylamine and then reducing it with a complex metal hydride; or (e) when $R_1$ represents hydrogen and X represents an ethylene group in a final product of general formula (I), reacting a compound of the general formula (VI) in which Y, $R_2$, $R_3$, $R_4$, $R_5$, $R_6$ and $R_7$ have the same meanings as above with an alkali or alkaline earth metal azide and then reducing it with a complex metal hydride; or (f) when $R_1$ represents hydrogen and X represents an ethylene group in a final product of general formula (I), reacting a compound of the general formula (VI) in which Y, $R_2$, $R_3$, $R_4$, $R_5$, $R_6$ and $R_7$ have the same meanings as above with ammonia under pressure and then reducing it with a complex metal hydride, whereafter, if desired, the compounds obtained of general formula (I) are converted in known manner into other compounds of general formula (I) or are converted with acids into salts and, if desired, a racemic mixture of compounds of general formula (I) is separated in known manner into the optically-active forms.

The reactive groups Y in compounds of general formulae (III) and (IV) are to be understood to be, for example, the residues of hydrohalic or sulphonic acids, such as the chloride, bromide, mesyloxy, tosyloxy, methylthio and methylsulphonyl groups, the chloride and bromide groups being preferred.

The protective groups B in compounds of general formula (III) can, in principle, be any of the conventional nitrogen protective groups. Such protective groups include, for example, benzyl and phthaloyl radicals, which are also especially preferred and which can be removed by hydrogenolysis or hydrazinolysis.

Reactions according to method (a) can be carried out in an inert solvent, for example dimethylformamide or acetonitrile, with the addition of a base. The reaction is preferably carried out in acetonitrile in the presence of potassium carbonate at 80° C.

In the case of reactions according to method (b), the use of a large excess of the amine component (V) is advantageous. The reaction can be carried out in an inert solvent, for example dimethyl sulphoxide, or with the use of a solvent at a temperature of from 20° to 120° C., for example in ethylenediamine at 118° C.

Reactive heterocycles A' in compounds of general formula (IV') are those, the hydroxyl or amino derivatives (IV') of which can participate in the Bucherer reaction (cf. The Merck Index, 9th edn., page ONR 15, pub. Rahway, New Jersey, U.S.A., 1976), for example indazoles and benztriazoles.

In the case of method (c), too, it is advantageous to use a large excess of the alkylenediamine (V), which is employed in the form of its salt with sulphurous acid. It is preferable to work in water or in a mixture of water and an alcohol, for example ethylene glycol or n-propanol, at reflux temperature.

The compounds of general formula (VI) can be produced by methods commonly found in the literature, but preferably by converting compounds of general formula (II) with substituted acetic anhydrides of the general formula (VII)

$$Y-CH_2-CO-NH-CO-CH_2Y \qquad (VII)$$

in which Y has the same meaning as above.

Complex metal hydrides such as $LiAlH_4$, $NaBH_4$, $KBH_4$, or $LiBH_4$ are utilized for reduction in processes (d), (e), and (f). $LiAlH_4$ is especially preferred.

Reaction with ammonia in process (f) is preferably conducted with liquid ammonia in an autoclave at moderate temperature.

The compounds of general formula (I) can, after the preparation thereof, be obtained directly as salts or, if desired, can be converted in known manner. Preferred examples of salts include the reaction products with hydrohalic acids, such as hydrochloric acid, or with oxalic acid.

Besides the compounds described in the following examples, the following compounds are also preferred:
4-(2-aminoethylamino)-3,5-dimethylisoxazole
4-(2-aminoethylamino)-3,5-dimethylpyrazole
4-(3-aminopropylamino)-1,3,5-trimethylpyrazole
4-(2-aminoethylamino)-1-carbamyl-3,5-dimethylpyrazole
4-(2-aminoethylamino)-1-(2-hydroxyethyl)-3,5-dimethylpyrazole
4-(2-aminoethylamino)-1-allyl-3,5-dimethylpyrazole
4-(2-aminoethylamino)-1-cyanomethyl-3,5-dimethylpyrazole
4-(2-aminoethylamino)-1-carboxamidomethyl-3,5-dimethylpyrazole
4-(2-aminoethylamino)-1-carboxymethyl-3,5-dimethylpyrazole
4-(2-aminoethylamino)-1-ethyl-3,5-dimethylpyrazole
4-(2-aminoethylamino)-3,5-dimethyl-1,2,4-triazole
6-(2-aminoethylamino)-1,2,4,5-tetramethyl-1,2,4-triazin-3-one
1-(2-aminoethylamino)-4-aminophthalazine
6-(2-aminoethylamino)-indazole
4-(2-aminoethylamino)-2-methylindazole The following examples are given for the purpose of illustrating the present invention:

EXAMPLE 1

4-(2-Aminoethylamino)-1,3,5-trimethylpyrazole 39.1 g. 4-(2-Phthalimidoethylamino)-1,3,5-trimethylpyrazole are boiled under reflux for 1 hour with 7 ml. hydrazine hydrate in 450 ml. ethanol. The reaction mixture is then acidified with 6N hydrochloric acid, boiled for a further hour and cooled to 10° C. The phthalyl hydrazide formed is filtered off with suction and the filtrate is evaporated. The residue obtained is dissolved in methanol and desalted with "Amberlite" IRA 400 (OH form). There are obtained 22.4 g. (100% of theory) 4-(2-aminoethylamino)-1,3,5-trimethylpyrazole in the form of an oil.

The 4-(2-phthalimidoethylamino)-1,3,5-trimethylpyrazole used as starting material is obtained in good yield by reacting 4-amino-1,3,5-trimethylpyrazole with N-(2-bromoethyl)-phthalimide in acetonitrile in the presence of potassium carbonate for 16 hours under reflux. It is obtained in the form of yellowish crystals which melt at 122°–123° C., after recrystallization from ethanol.

EXAMPLE 2

4-(2-Aminoethylamino)-3,5-dimethyl-1-phenylpyrazole

This is obtained in a yield of 83% of theory in the form of a light brownish colored oil in a manner analogous to that described in Example 1 by the hydrazinolysis of 4-(2-phthalimidoethylamino)-3,5-dimethyl-1-phenylpyrazole.

The benzoate is obtained in the form of colorless crystals which, after recrystallization from ethyl acetate, melt at 136°–138° C.

The 4-(2-phthalimidoethylamino)-3,5-dimethyl-1-phenylpyrazole used as starting material is obtained in a manner analogous to that described in Example 1 by reacting N-(2-bromoethyl)-phthalimide with 4-amino-3,5-dimethyl-1-phenylpyrazole. After chromatographic purification on a silica gel column (methylene chloride-ethyl acetate 6:4 v/v), it is obtained in a yield of 56% of theory in the form of a light brownish colored oil.

EXAMPLE 3

3-(2-Aminoethylamino)-1,2,4-trimethylpyrazol-5-one 24.7 g. 3-Chloro-1,2,4-trimethylpyrazol-5-one are boiled under reflux for 22 hours in 157 ml. ethylenediamine. The reaction mixture is then evaporated and the residue is dissolved in methanol and desalted with the ion exchanger "Amberlite" IRA 400 (OH form). The eluate is evaporated and the residue is taken up in methylene chloride and purified on a silica gel column using, as elution agent, methylene chloride-methanol (ammonia-saturated) 8:2 v/v. There are obtained 23 g. (81% of theory) 3-(2-aminoethylamino)-1,2,4-trimethylpyrazol-5-one in the form of a yellowish oil.

The 3-chloro-1,2,4-trimethylpyrazol-5-one used as starting material can be obtained in the following manner: 28.6 g. 3-hydroxy-1,2,4-trimethylpyrazol-5-one (m.p. 87°–89° C., after recrystallization from ethyl acetate), prepared from diethyl methylmalonate and N,N'-dimethylhydrazine, are boiled under reflux for 3.5 hours with 55 ml. phosphorus oxychloride. The reaction mixture is then evaporated and the residue is stirred with ice and water, rendered alkaline by the addition of 10N aqueous sodium hydroxide solution and extracted 8 times with 100 ml. amounts of methylene chloride. The combined extracts are then dried and evaporated to give 24.7 g. (76.5% of theory) 3-chloro-1,2,4-trimethylpyrazol-5-one in the form of colorless crystals; m.p. 37°–38° C.

EXAMPLE 4

4-(2-Aminoethylamino)-indazole

Sulphur dioxide is passed into a mixture of 66 ml. ethylenediamine and 146 ml. water until the pH is 7–8, whereupon 13.4 g. 4-hydroxyindazole are added thereto and the reaction mixture heated, with stirring, to 100°–110° C. for 1 hour. After cooling, the reaction mixture is mixed with 300 ml. methanol and the salts formed are filtered off with suction and washed with methanol. The solution is gently concentrated in a vacuum to 50 to 100 ml. and the N,N'-bis-(indazolyl-4)-ethyldiamine formed as by-product is filtered off with solution. The filtrate is then rendered alkaline with a concentrated aqueous solution of ammonia and extracted 10 times with methylene chloride. The combined extracts are dried and concentrated to about 100 ml. There are obtained 7.6 g. (43% of theory) of 4-(2-aminoethylamino)-indazole in the form of pale beige crystals; m.p. 138°–140° C.

The corresponding benzoate is obtained in the form of colorless crystals which melt, with decomposition, at 178°–180° C., after recrystallization from isopropanol.

EXAMPLE 5

4-(3-Aminopropylamino)-indazole

Sulphur dioxide is passed into a solution of 74 g. 1,3-diaminopropane in 150 ml. water until the pH is 7, whereupon 13.4 g. 4-hydroxyindazole are added thereto and the reaction mixture heated to 100° C. for 3 hours. Salts are precipitated out by the addition of double the amount of methanol and then filtered off with suction. The filtrate is evaporated and the oily residue rendered alkaline with a concentrated aqueous solution of ammonia, followed by extraction with methylene chloride. By concentration of the extract, there are obtained 7.8 g. (41% of theory) 4-(3-aminopropylamino)-indazole in the form of grey crystals; m.p. 154°–163° C.

EXAMPLE 6

5-Methyl-4-(2-aminoethylamino)-indazole

A mixture of 15.3 g. 4-amino-5-methylindazole (m.p. 197°–200° C., prepared by the reduction of 4-nitro-5-methylindazole), 146 g. ethylenediamine sulphite, 146 ml. ethylene glycol and 146 ml. water is stirred for 24 hours at 110° C. After cooling, the reaction mixture is mixed with 500 ml. methanol and the precipitated salts are filtered off with suction and then washed with methanol. The filtrate is allowed to run through the ion exchanger "Amberlite" 120 (H+ form), which is subsequently washed with methanol, and the amine is liberated by the addition of methanolic ammonia. The eluate is evaporated and the residue is dissolved in methylene chloride-methanol (9:1 v/v) and chromatographed on a silica gel column with the elution agent methylene chloride-methanol (9:1 v/v). There are obtained 6.1 g. (31% of theory) 5-methyl-4-(2-aminoethylamino)-indazole in the form of beige crystals; m.p. 153°–155° C.

EXAMPLE 7

5-(2-Aminoethylamino)-indazole

A mixture of 12.0 g. 5-aminoindazole, 146 g. ethylenediamine sulphite, 146 ml. water and 10 ml. n- propanol is stirred for 24 hours at 100° C. After cooling, the reaction mixture is diluted with 500 ml. methanol. The precipitated salts are filtered off with suction and the filtrate is evaporated. The residue is rendered alkaline by the addition of a concentrated aqueous solution of ammonia. After suction filtration and washing with water there are obtained 9.4 g. (59% of theory) of crystalline 5-(2-aminoethylamino)-indazole; m.p. 150°–165° C.

EXAMPLE 8

7-(2-Aminoethylamino)-indazole 13.4 g. 7-Hydroxyindazole are heated to 110° C. for 2 to 3 hours, while stirring, with 146 g. ethylenediamine sulphite in 146 ml. water. The N,N'-bis-indazolyl-(7)-ethylenediamine formed as by-product is filtered off from the hot reaction mixture and washed with a little water and the salts are precipitated out from the filtrate by adding a 5 fold amount of methanol and washed with methanol. The filtrate is evaporated to a viscous consistency, rendered alkaline with a concentrated aqueous solution of ammonia, cooled with ice, filtered with suction and washed with a little water. There are obtained 11.8 g. of 7-(2-aminoethylamino)-indazole in the form of bright yellowish crystals which sinter at 163° C. and melt at 165°–167° C. Colorless crystals (m.p. 166°–168° C.) are obtained by recrystallization from ethyl acetate-isopropanol.

EXAMPLE 9

4-(2-Aminoethylamino)-benztriazole 13.3 g. 4-Hydroxybenztriazole (very impure) are stirred for 2 hours at 100°–110° C. with 146 g. ethylenediamine sulphite in 146 ml. water. After cooling, the reaction mixture is mixed with 500 ml. methanol, the salts formed are filtered off with suction and the filtrate is desalted with the ion exchanger "Amberlite" IRA 400 (OH form) which has been pretreated with ammonium carbonate. The eluate is evaporated and the solidified mass obtained is triturated with a little concentrated aqueous ammonia solution. The solid material is filtered off with suction and then washed with a little water. There is obtained 1.7 g. (10% of theory) 4-(2-aminoethylamino)-benztriazole in the form of beige crystals; m.p. 181°–183° C.

A sesquioxalate can be obtained from ethanolic solution by adding oxalic acid; beige crystals, m.p. 169°–171° C. (decomp.).

EXAMPLE 10

4-(2-Amino-ethylamino)-3,5-dimethyl-1-allyl-pyrazole is prepared as in Example 1 by the hydrazinolysis of 20 g of 4-(2-phthalimido-ethylamino)-3,5-dimethyl-1-allyl-pyrazole. The desired product is obtained subsequent to column-chromatography purification on silica gel (methanol saturated with NH$_3$/dichloromethane 10:1 v/v).

Yield: 7.4 g (61% theor.) of yellow oil.

Benzoate: colorless crystals, f.p. 76°–77° C. (glacial acetic acid/ether).

The starting compound 4-(2-phthalimido-ethylamino)-3,5-dimethyl-1-allyl-pyrazole, is obtained as in Example 1 by reacting N-(2-bromoethyl)-phthalimide with 4-amino-3,5-dimethyl-1-allyl-pyrazole. A slightly brownish oil (24% theor.) is obtained subsequent to purification on silica gel (dichloromethane and ethyl acetate 7:3 v/v).

The starting compound 4-amino-3,5-dimethyl-1-allyl-pyrazole, is obtained by reducing 59 g of 4-nitro-3,5-dimethyl-1-allyl-pyrazole with 72 g of powdered iron in 600 ml of methanol and 390 ml of concentrated HCl. After 2.5 h of reflux distillation the undissolved components are suctioned off and concentrated by evaporation. The resulting oil is dissolved in water alkalized with NaOH and the precipitated substance suctioned off and extracted with dichloromethane. The extracts are dried and concentrated by evaporation.

Yield: 40 g (81% theor.) of a thin light-brown oil.

Oxalate: colorless crystals, f.p. 183°–184° C. (ethanol).

The starting compound 4-nitro-3,5-dimethyl-1-allyl-pyrazole is obtained by allylizing 30 g of 4-nitro-3,5-dimethyl-pyrazole in 150 ml of DMF with 22 ml of 3-bromopropene-1 at room temperature in the presence of 35 g of potassium carbonate. This is followed by 30 minutes of reflux distillation, suctioning, and concentration by evaporation.

Yield: 38 g of a thin, light-brown oil.

EXAMPLE 11

4-(2-Amino-ethylamino)-3,5-dimethyl-1-propyl-pyrazole is prepared as in Example 1 by the hydrazinolysis of 34.6 g of 4-(2-phthalimido-ethylamino)-3,5-dimethyl-1-propyl-pyrazole.

Yield: 20.5 g (100% theor.) of a slightly brownish oil.

Benzoate: colorless crystals, f.p. 113°–114° C. (ethyl acetate).

The starting compound 4-(2-phthalimido-ethylamino)-3,5-dimethyl-1-propyl-pyrazole is obtained as in Example 1 by reacting 97 g of N-(2-bromoethyl)-phthalimide with 48.5 g of 4-amino-3,5-dimethyl-1-propyl-pyrazole. Purification is by column chromatograph on silica gel (dichloromethane and ethyl acetate 8:2 v/v).

Yield: 34.6 g (30% theor.) of a brownish oil.

The starting compound 4-amino-3,5-dimethyl-1-propyl-pyrazole is obtained by catalytically reducing 38.5 g of 4-nitro-3,5-dimethyl-1-allyl-pyrazole in 600 ml of methanol on 3 g of Raney nickel. Hydrogenation is stopped after about 6 h and the material is suctioned off from the catalyst and concentrated by evaporation.

Yield: 32.1 g (100% theor.) of a thin yellow oil.

EXAMPLE 12

5-(2-Amino-ethylamino)-1,4-dimethyl-pyrazole 6.8 g of 5-(2-phthalimido-ethylamino)-1,4-dimethyl-pyrazole are dissolved in 100 ml of ethanol and the solution reflux distilled for 2 h subsequent to the addition of 1.75 ml of hydrazine hydrate. The mixture is allowed to cool, the precipitated phthalohydrazide suctioned off, and the filtrate concentrated by evaporation.

Yield: 3.6 g (colorless oil).

The starting compound 5-(2-phthalimido-ethylamino)-1,4-dimethyl-pyrazole is obtained by reacting 5-amino-1,4-dimethyl-pyrazole with N-(2-bromoethyl)-phthalimide.

M.p. 124°–126° C. (isopropyl ether).

EXAMPLE 13

5-(2-Benzylamino-ethylamino)-1,4-dimethyl-pyrazole

1st Stage: 5-(Chloracetamido)-1,4-dimethyl-pyrazole 27 g of 5-amino-1,4-dimethyl-pyrazole are dissolved in 290 ml of absolute dichloromethane. 50 g of chloroacetic acid anhydride is added and the mixture stirred for 3 h at room temperature. The dichloromethane phase is then washed with a saturated sodium-hydrogencarbonate solution and water, dried over sodium sulfate, and concentrated by evaporation. The residue is recrystallized from isopropyl ether.

M.p. 75° C.

Yield: 35.4 g (75% theor.).

2nd Stage:
5-(Benzylamino-acetamido)-1,4-dimethyl-pyrazole 35 g of 5-(chloroacetamido)-1,4-dimethyl-pyrazole are dissolved in 300 ml of absolute dimethyl formamide and the solution, subsequent to the addition of 46 g of benzylamine, heated to 100° C. for 3 h. The cooled solution is diluted with water and extracted with dichloromethane. The dichloromethane phase is washed with a saturated table-salt solution, dried on sodium sulfate, and concentrated by evaporation. The residue is recrystallized from ethyl acetate.

M.p. 114° C.

Yield: 27.5 g (57% theor.).

3rd Stage:
5-(2-Benzylamino-ethylamino)-1,4-dimethyl-pyrazole 14.8 g of 5-benzylamino-acetamido)-1,4-dimethyl-pyrazole are dissolved in 150 ml of absolute tetrahydrofuran and dripped at room temperature into a stirred suspension of 2.4 g of LiAlH$_4$ in 50 ml of absolute tetrahydrofuran. After addition is stopped, stirring is continued for 4 h at room temperature, the reaction mixture cooled to 0° C., carefully treated with ice water, acidified with 2N sulfuric acid to pH 5, and suctioned off. The filtrate is treated with concentrated ammonia and extracted with ethyl acetate. The ethyl acetate phase is dried over sodium sulfate and concentrated by evaporation in the vacuum. 13.5 g (96% theor.) of 5-(2-benzylamino-ethylamino)-1,4-dimethyl-pyrazole are obtained in the form of a viscous oil.

The processes specified are repeated with an appropriately substituted 5-amino-1-alkyl-4-methyl-pyrazole, obtaining the corresponding substituted 5-(2-benzylamino-ethylamino)-1-alkyl-4-metyl-pyrazole.

Table I lists the intermediate products of Stage 1 of the overall process, Table II those of Stage 2, and Table III those of Stage 3.

TABLE I

ClCH$_2$—C(=O)—HN— [1,4-dimethyl-pyrazole with R$_3$']

| R$_3$' | M.P. (°C.) | Yield (%) | Recryst. Solvent |
|---|---|---|---|
| 13a I —CH$_2$—C$_6$H$_5$ | 126 | 94 | Isopropyl ether |
| 13b I cyclohexyl | 124–126 | 60 | Isopropyl ether |
| 13c I —CH$_2$—CH$_2$—CH$_3$ | 80 | 77 | Isopropyl ether |
| 13d I —CH$_2$—CH(CH$_3$)$_2$ | 84 | 73 | |

TABLE II

C$_6$H$_5$—CH$_2$—HN—CH$_2$—C(=O)—HN— [1,4-dimethyl-pyrazole with R$_3$']

| R$_3$' | M.P. (°C.) | Yield (%) | Recryst. Solvent |
|---|---|---|---|
| 13a II —CH$_2$—C$_6$H$_5$ | 115 | 82 | Isopropyl ether |
| 13b II cyclohexyl | 95–96 | 70 | Isopropyl ether |
| 13c II —CH$_2$—CH$_2$—CH$_3$ | Oil | 90 | |
| 13d II —CH$_2$—CH(CH$_3$)$_2$ | Oil | 90 | |

TABLE III

C$_6$H$_5$—CH$_2$—HN—CH$_2$—CH$_2$—NH— [1,4-dimethyl-pyrazole with R$_3$']

| R$_3$' | M.P. (°C.) | Yield (%) |
|---|---|---|
| 13a III —CH$_2$—C$_6$H$_5$ | Oil | 89 |
| 13b III cyclohexyl | Oil | 87 |
| 13c III —CH$_2$—CH$_2$—CH$_3$ | Oil | 70 |

TABLE III-continued $$C_6H_5{-}CH_2{-}HN{-}CH_2{-}CH_2{-}NH\begin{array}{c}CH_3\\|\\\diagup\diagdown\\|\phantom{xx}\|\\N\diagdown\phantom{x}N\\|\\R_3'\end{array}$$

| | $R_3'$ | M.P. (°C.) | Yield (%) |
|---|---|---|---|
| 13d III | $-CH_2-CH\diagup^{CH_3}_{\diagdown CH_3}$ | Oil | 67 |

EXAMPLE 14

5-(2-amino-ethylamino)-1-benzyl-4-methyl-pyrazole
23.6 g of
5-(chloracetamido)-1-benzyl-4-methyl-pyrazole (manufactured as in Ex. 13, St. 1) are dissolved in 240 ml of dimethyl formamide. 6.4 g of sodium azide are added and the solution stirred 6 h at room temperature. The reaction mixture is diluted with water and extracted by shaking with dichloromethane. The dichloromethane phase is washed with water, dried on sodium sulfate, and concentrated by evaporation. The residue is recrystallized with isopropyl ether, yielding 21.8 g (90% theor.) of
5-(azido-acetamido)-1-benzyl-4-methyl-pyrazole with a melting point of 105° C.

This is dissolved in 220 ml of absolute tetrahydrofuran and the solution dripped into a stirred suspension of 4.6 g of $LiAlH_4$ in 100 ml of absolute tetrahydrofuran. Addition is stopped and the stirring continued for 6 h at room temperature. The material is then cooled to 0° C., carefully treated with ice water, and acidified with sulfuric acid to pH 6. Suctioning off is followed by treating the filtrate with concentrated ammonia and shaking with ethyl acetate. The ethyl acetate phase is washed with water, dried on sodium sulfate, and concentrated by evaporation. The oily residue is purifed by chromatography in a silica-gel column.

Yield: 12 g (65% theor.) of a colorless oil.

EXAMPLE 15

5-(2-Amino-ethylamino)-1,4-dimethyl-pyrazole 20 g of 5-(chloroacetamido)-1,4-dimethyl-pyrazole (manufactured as in Ex. 13, St. 1) are dissolved in 250 ml of methanol and, subsequent to the addition of 250 ml of liquid ammonia, heated to 70° C. for 8 h in an autoclave. The material is concentrated by evaporation, the residue dissolved in water, and the solution passed through a basic ion exchanger.

The eluate is concentrated by evaporation, yielding 17.5 g of an oily residue, which is dissolved in 150 ml of absolute tetrahydrofuran. The solution is dripped at room temperature into a suspension of 3.5 g of $LiAlH_4$ in absolute tetrahydrofuran. After addition is stopped, stirring is continued for 6 h at room temperature, the material cooled to 0° C., carefully treated with ice water, acidified with dilute sulfuric acid to pH 6, and suctioned off. The filtrate is treated with concentrated ammonia and shaken out several times with ethyl acetate. The combined ethyl acetate phases are washed with water, dried on sodium sulfate, and concentrated by evaporation, yielding 12.4 g (78% theor.) of a colorless oil.

The following examples illustrates the use of the novel intermediates in making cardioactive end products which can be administered in the same dosage and form as the compounds of Federal Republic of Germany Patent Specification Nos. 28 19 629 and 28 44 497, except that it is possible to use even lower dosages if desired because of their greater activity:

EXAMPLE 16

1-Phenoxy-3-[2-(1,3,5-trimethylpyrazol-4-ylamino)ethylamino]-propan-2-ol 3.8 g. Phenyl glycidyl ether are left to stand for 48 hours at ambient temperature with 8.4 g. 4-(2-aminoethylamino)-1,3,5-trimethylpyrazole. The reaction mixture is then dissolved in methylene chloride, shaken out with water, dried and purified chromatographically with silica gel, using methylene chloride-ammoniacal methanol (92:8 v/v) as elution agent. After evaporation of the pure fractions, there are obtained 4.7 g. (59% of theory) of the desired free base in the form of an oil.

This oily base is dissolved in ethyl acetate, 1.7 g. fumaric acid is added thereto and the initially greasy precipitate is triturated with isopropyl alcohol and recrystallized from ethanol to give the corresponding fumarate in the form of colorless crystals; m.p. 124° C. (decomp.).

The 4-(2-aminoethylamino-1,3,5-trimethylpyrazole used as starting material can be obtained as follows: 4-amino-1,3,5-trimethylpyrazole is reacted with N-(2-bromoethyl)-phthalimide in the presence of potassium carbonate in acetonitrile under reflux for 16 hours to give a good yield of 4-(2-phthalimidoethylamino)-1,3,5-pyrazole in the form of yellowish crystals which, after recrystallization from ethanol, melt at 122°–123° C. After subsequent hydrazinolysis, there is obtained 4-(2-aminoethylamino)-1,3,5-trimethylpyrazole in the form of an oil.

It will be appreciated that the instant specification and examples are set forth by way of illustration and not limitation, and that various modifications and changes may be made without departing from the spirit and scope of the present invention.

We claim:

1. An N-pyrazolylalkylenediamine of the formula

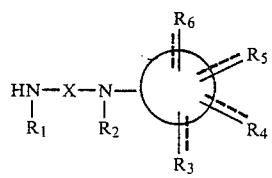

wherein $R_1$ and $R_2$ each independently is hydrogen, an alkyl radical containing up to 6 carbon atoms, or a benzyl radical, X is an alkylene radical containing 2 to 6 carbon atoms, A is a pyrazol-4-yl or a pyrazol-5-yl radical, $R_3$, $R_4$, $R_5$ and $R_6$ each independently is hydrogen, or an alkyl radical containing up to 6 carbon atoms, which can be substituted by hydroxyl, carbamyl, $C_3$–$C_8$ cycloalkyl-, nitrile or carboxyl, an alkenyl radical containing 2 to 6 carbon atoms, a phenyl or carbamyl radical, or a salt thereof.

2. A compound or salt according to claim 1, in which X has 2 or 3 carbon atoms.

3. A compound or salt according to claim 1, in which $R_1$ and $R_2$ are hydrogen.

4. A compound or salt according to claim 1, in which $R_1$ is benzyl.

5. A compound according to claim 1, wherein such compound is 4-(2-aminoethylamino)-1,3,5-trimethylpyrazole or a salt thereof.

* * * * *

UNITED STATES PATENT AND TRADEMARK OFFICE
CERTIFICATE OF CORRECTION

PATENT NO. : 4,507,488
DATED : March 26, 1985
INVENTOR(S) : Fritz Wiedemann, et al It is certified that error appears in the above-identified patent and that said Letters Patent is hereby corrected as shown below:

| | |
|---|---|
| Col. 2, line 1 | Before "-hexyl" delete "n" and substitute --n-- |
| Col. 2, line 10 | Delete "intermediate" and substitute --intermediates-- |
| Col. 2, line 50 | Delete formula and substitute 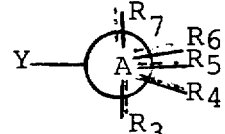 |
| Col. 3, line 5 | Delete "A" inside of ring and substitute --A'-- |
| Col. 4, line 18 | Delete "n-" and substitute --n- -- |
| Col. 6, line 17 | Delete "solution" and substitute --suction-- |
| Col. 6, line 68 | Delete "n-" and substitute --n- -- |
| Col. 12, line 3 | Delete "examples" and substitute --example-- |

Signed and Sealed this

Twentieth Day of August 1985

[SEAL]

Attest:

DONALD J. QUIGG

Attesting Officer  Acting Commissioner of Patents and Trademarks